United States Patent [19]

Javan

[11] 3,998,557
[45] Dec. 21, 1976

[54] GAS DETECTOR
[75] Inventor: Ali Javan, Boston, Mass.
[73] Assignee: Massachusetts Institute of Technology, Cambridge, Mass.
[22] Filed: June 3, 1974
[21] Appl. No.: 475,775
[52] U.S. Cl. .............................. 356/205; 356/178; 331/94.5 C
[51] Int. Cl.² ..................... G01N 21/22; G01J 3/46
[58] Field of Search .......... 331/94.5; 356/201, 204, 356/205, 206, 88, 178; 250/573

[56] References Cited
UNITED STATES PATENTS

| 3,492,600 | 1/1970 | Zitter | 331/94.5 M |
| 3,504,977 | 4/1970 | Matthews | 356/89 |
| 3,609,587 | 9/1971 | Kolb | 331/94.5 T |
| 3,843,258 | 10/1974 | Shupe | 356/88 |

OTHER PUBLICATIONS
Helvig et al.; "Frequency Stability of Methane Stabilized He–Ne Lasers," J. Appl. Phys., vol. 43, No. 2.

Primary Examiner—John K. Corbin
Assistant Examiner—Conrad Clark
Attorney, Agent, or Firm—Arthur A. Smith, Jr.; Robert Shaw; John N. Williams

[57] ABSTRACT

Laser detector for gases employs two beams, one at wave length corresponding to an optical absorption resonance of the gas to be detected, 3.39 micron in the preferred methane detector, and another at a similar wave length, but lying outside of the effective absorption curve, with a balance circuit for detection. The embodiments show common beam path, common lasing medium and common power sources for generating the two beams. In one embodiment two resonant cavities share a common discharge tube and output mirror through switching, while in others the resonators are separate but sharing the same gas system or power supply. A suppression cell filled with methane is employed to suppress a dominant transition, to establish lasing at another transition, and adjustable length and adjustable pressure cells are also employed to enable balancing of the system prior to detection.

20 Claims, 6 Drawing Figures

GAS DETECTOR

This invention relates to the detection of gases using lasers.

Since the early days when the laser became a reality, one of my research objectives has been to exploit lasers in highly sensitive and precise spectroscopic observations. A great deal has evolved over the past decade of efforts. By now, laser spectroscopy has become a firmly established field and is the subject of many published papers. Its range of applications extends from highly precise observations, with accuracies surpassing, e.g., one part in $10^{12}$, to highly sensitive detection methods, enabling, e.g., remote detection of small traces of elements at extremely low concentrations — $10^4$ atoms/cc — at a distance of about one hundred kilometers.

In laser spectroscopy, the monochromaticity of laser radiation, along with its high-field intensity, plays the major role. The former feature is responsible for high-resolution and the latter for high-detection sensitivity.

In the early spectroscopic observations, a number of atomic transitions--in particular, the He-Ne laser--were used to test and devise the necessary methods of observation. The transitions explored were those which were used to obtain the laser oscillations at the various wavelengths. In subsequent experiments, starting late in 1963, the output of a He-Ne laser oscillating on its 3.39 micron infrared laser line was used to perform spectroscopic observations on gas samples external to the laser. The gases consisted of a number of organic molecules whose C-H stretching mode of vibration resulted in rotation-vibration absorption bands lying in the 3.39 micron region. In these experiments the He-Ne laser frequency was tuned over a limited range by application of a tunable magnetic field obtained from a solenoid. The molecular gas samples at low gas pressures were subjected to the laser output. This enabled observation of absorption lines as the laser frequency was scanned across their linewidths.

Among various gases studied in these early experiments, methane showed the strongest absorption lines, one of them lying sufficiently close to the peak of the 3.39 micron laser transition to enable observation of the absorption effect without requiring magnetic field laser-frequency tuning. Reference is made to Physics of Quantum Electronics, edited by P. L. Kelley, B. Lux, and P. E. Tannanwald, McGraw Hill Book Co., 1966, in particular, "Spectroscopy with Gas Lasers", Feld, Parks, Schlossberg, and Javan, p. 567 et seq., and "Tuned-Laser Spectroscopy of Organic Vapors," Gerritsen, p. 581 et seq.

The objects of the present invention include the provision of a laser detector useful as a practical tool for field operation in the detection of gas quantities as small as 1 ppm or less at atmospheric pressure or in air where the absorption line widths are very broad and therefore present difficulties if the usual scanning techniques are employed. A specific object is to provide a reliable methane detector for field use.

According to one aspect of the invention, through lasing, two beams are produced, the beams preferably being related or having at least some source variations correlated. The first beam has a wavelength corresponding to a given absorption resonance (for methane the 3.39 micron resonance), and the other beam, a reference beam, is not subject to absorption. The two beams are detected, after at least the first beam has, or advantageously both have, transited a volume in which the gas to be detected may reside, and the detected quantities compared, as by a bridge circuit, the comparison indicating whether or not or to what extent the subject gas is present. Preferably, with both beams passing through the same path, provision is made, as by rapid switching, whereby during the period of transit of any scattering particle through the volume, both beams are affected, whereby the scattering effects can be cancelled through the comparison operations.

In preferred embodiments both beams transit the same optical path as a result of switching or chopping, and the beams are preferably detected by a common detector. In the various cases in which both beams pass through the sensed volume, the wavelength of the second beam is selected to lie outside the effective absorption curve of the gas to be detected.

While the beams may be related in a number of different ways, it is preferred that they be generated using the same power source. Preferably, in using gas lasers, the gas pressure is also made to be the same for generating both beams. In one particularly preferred embodiment a common laser medium is employed for two different laser cavities, which are optically or mechanically switched. Preferably both cavities have a common mirror through which their output beams alternately pass in the same path. In another embodiment, different portions of a confined gas mass lase to produce the different beams, open communication between the regions assuring that pressure variations affect both regions in similar ways. Beam combiner means preferably enabled both beams, alternately chopped, to pass through the same path through the gas volume to the detector.

Preferably, whether common or not, the same kind of lasing medium is employed to produce both beams, preferably from the same upper energy state, and a selective suppressor is employed for one beam, to suppress the transition that otherwise would tend to be dominant, thus to enable a different transition to dominate and produce a wavelength offset from the normally dominant radiation.

In the preferred methane detector according to the invention, methane itself is confined in a suppression cell and interposed in one of the cavities. It effectively absorbs the 3.39 micron radiation (corresponding to the $3s_2$ to $3s_4$ transition) to the extent that the $3s_2$ to $3p_4$ transition becomes dominant, generating radiation outside of the absorbance curve of methane.

Advantageously, according to the invention, parameters of the suppressor or of an additional balancing cell are variable for balancing the detector. In the case of methane or other effective cell, its length is variable, as by moving narrower or wider portions of the cell into the cavity axis.

Alternately, with gas medium, the pressure is variable, thus to increase or decrease the amount of absorption.

In another preferred embodiment modulation is employed to produce the second beam and superheterodyne detection techniques are employed.

These and other objects and features of the invention will be understood from the following description of preferred embodiments taken in conjunction with the drawings wherein.

The invention will be illustrated as applied to methane detectors.

As noted above, it is well known that methane gas has a strong absorption resonance in close coincidence with the 3.39 micron He-Ne laser line, see article entitled "Tuned-Laser Spectroscopy of Organic Vapor", Gerritsen, Physics of Quantum Electronics, McGraw Hill Book Co., 1966. The absorption resonance in methane belongs to its P (7) line of the $V_3$ band and the He-Ne transition is the ($3s_2$ to $3p_4$) transition in Ne. The absorption coefficient of methane resonance in pure methane is about 0.2/cm. torr. In the atmosphere, however, the absorption coefficient at 1-torr methane partial pressure is about $6 \times 10^{-3}$/cm. per torr of methane.

According to the preferred embodiment of the present invention, a highly sensitive detector device is made by subjecting the sample gas containing methane to two radiation beams of equal intensities but slightly different wavelenghts, one of them lying within the linewidth of the methane resonance and the other lying outside of the resonance linewidth. The presence of methane in this case would mainly attenuate the resonant beam, resulting in an imbalance in the intensities of the two beams. A balanced differential detection system can then be used to detect traces of methane. The detection system will be particularly sensitive if the intensity drifts and fluctuations of the two beams relative to one another are kept at a minumum, by relating the beams in various ways. Note further that for both beams propagating colinearly through air, effects such as scattering from dust particles, wind, and smoke will attenuate both beams similarly and hence will not appear as a signal at the output of an appropriately designed balanced-differential electronic system. Such a detection system will only respond if one of the beams is attenuated and not the other.

The lower level of the 3.39 micron He-Ne laser transition, the $3p_4$ level of neon, is very close to another neon level, the $3p_2$ level. The spacing between these two levels is 0.88 cm$^{-1}$ (26 KMHz). The $3s_2$ to $3p_2$ transition in neon is a allowed transition and differs from the well-known 3.39 micron He-Ne laser transition, the $3s_2$ to $3s_4$, by the 0.88 cm$^{-1}$ difference, approximately 3 times the linewidth of the methane resonance.

In fact, in a He-Ne gas-discharge laser, the $3s_2$ to $3s_{p2}$ transition has inverted population and is hence an amplifying transition with a sizeable gain. In a He-Ne laser, however, the $3s_2$ to $3p_4$ transition has a somewhat larger oscillator strength (or matrix element) compared to the $3s_2$ to $3p_2$ transition. As a result, under normal circumstances oscillation build-up occurring in the $3s_2$ to $3p_4$ transition inhibits oscillation in the $3s_2$ to $3p_2$ line.

Figure 1:
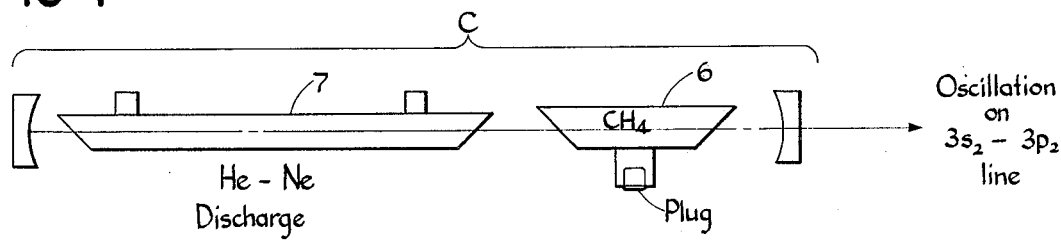
FIG. 1 is a diagrammatic view of a helium-neon laser employing a methane cell as a suppressor to suppress the normally dominant transition $3s_2$ to $3s_4$ thereby to produce the transition $3s_2$ to $3s_2$.

Referring to FIG. 1, this competition is reversed by placing inside the laser cavity, in addition to the He-Ne discharge tube 7, another cell 6 containing methane gas. In this case, the methane resonance described above introduces sufficient absorption at the $3s_2$ to $3p_4$ transition to prevent the laser oscillation from occurring on the $3s_2$ to $3p_4$ line. This will in turn result in oscillation to take place on the nearby $3s_2$ to $3p_2$transition.

With the above background, several specific types of methane detector systems will be described.

Type I.

Figure 2:
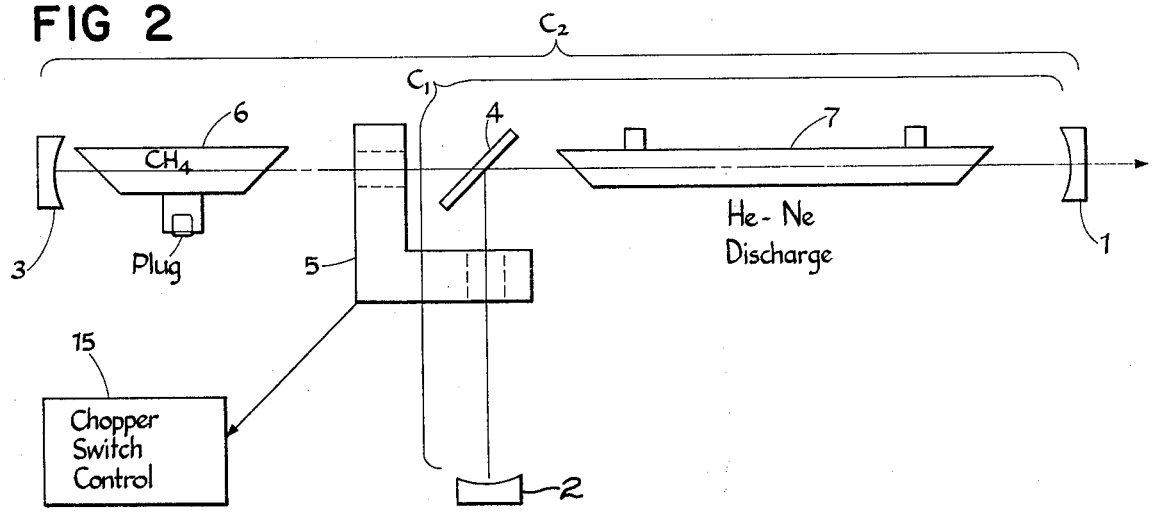
FIG. 2 is a block diagram of a multiple cavity laser system for use in a preferred embodiment.

Referring to FIG. 2, it is advantageous to the same He-Ne laser discharge tube 7 to produce both $3s_2$ to $2p_4$ and $3s_2$ to $2p_2$ laser oscillation, by switching between two different cavities $C_1$ and $C_2$. The intensity drifts and fluctuations of both beam, due to power source variations, gas pressure, temperature, etc., will be the same and hence will cancel out in the balanced detection system. Usually the troublesome drifts happen to be long-term drifts. For instance, power supply variation happens over a period of several seconds, or a second or a tenth of a second. A 100 Hz switching frequency is good enough to eliminate such fluctuation. 60 Hz noise also is a major source of problems. Again by using a 100 Hz detection system and narrow banding the detection around 100 Hz, the 60 cycle noise cancels out very smoothly.

In the embodiment of FIG. 2, mirrors 1, 2, and 3 are of high reflectance at 3.39 micron. The beam splitter 4 divides the resonator in two parts: in one part, in resonator cavity $C_1$, the beam splitter 4 acts as a lossy reflector between mirrors 1, 2; in the other part, in resonator cavity $C_2$, the beam splitter 4 acts as a lossy transmission element between mirrors 1, 3. The chopper switch 5 is either a mechanical chopper or an electro-optical switch.

As an example of a mechanical chopper one may employ a motor driving a rotating blade which alternately interrupts the paths of the two resonator cavities, C and $C_2$.

As an example of an electro-optical switch, one can use gallium arsenide, which is transparent at 3.39 micron.

This being a Brewster angle system, the electro-optical modulator switches the polarization of the light as it goes through in the known manner when an electrical field is applied. The electric field applied to the electro-optical switch tilts the direction of polarization and makes the resonator lossy to radiation of a given polarization, effectively switching the cavity resonators (1, 4, 2) and (1, 4, 3) on and off. This is done at an audio-frequency, the two resonators being switched on and off out of phase with respect to each other, i.e. when (1, 4, 2) is on, (1, 4, 3) is off, and vice versa.

The methane cell 6 in (1, 4, 3) resonator is similar in construction to the He-Ne discharge cell. Its Brewster-angle windows are transparent at 3.39 micron. Within this cell methane is provided at a pressure of several torrs. The particular pressure depends on the length of the cell. If one provides the gas at a pressure of 4 or 5 torrs in a cell of length of approximately 10 cm., it will perform adequately if the He-Ne laser has a length of about 60 – 70 cm. For a given geometry, the parameters for the cell are to be calculated by consideration of the size of the relative gain for 3.39 at the two transitions, $3s_2$ to $3p_4$ and $3s_2$ to $3p_2$, absorption of methane, .2/cm. /torr.

Figure 3:
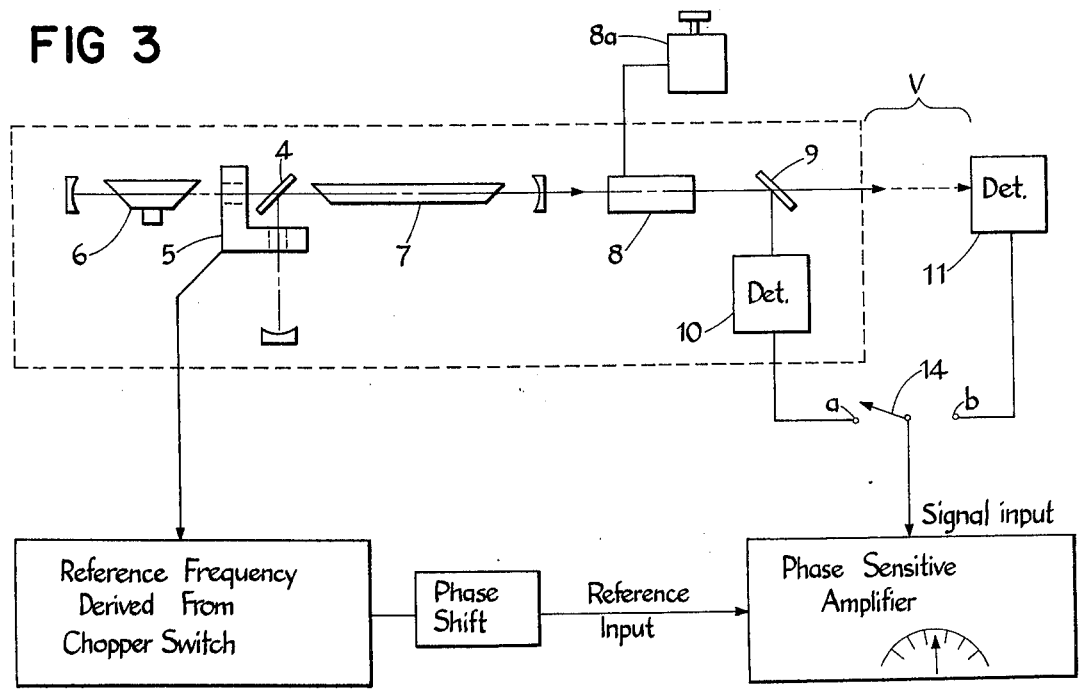
FIG. 3 is a block diagram of the complete detector incorporating the laser system of FIG. 2.

When the cavity $C_1$ (1, 4, 2) is switched off, the laser oscillates on $3s_2 \rightarrow 3p_2$ line; on the other hand, with cavity $C_2$ (1, 4, 3) switched off, the laser oscillates on the usual 3.39 micron line, i.e. $3s_2 \rightarrow 3p_4$ line. By energizing the optical switch at audio frequency by control 15, the laser output, coupled out through, e.g. mirror 1, will alternately switch at the selected frequency between the two laser frequencies, one of them lying at a frequency close to the peak of the methane absorption line-width. Referring to FIG. 3 the laser output after transiting volume V in which the gas to be detected may be present is detected in an infrared detector 11 and fed to a phase-sensitive amplifier 13 (i.e., the well known lock-in amplifier see for instance *Microwave Spectroscopy of Gases* C. H. Townes and A. L. Schawlow, McGraw Hill Book Co.) synchronized at the frequency of the chopper switch 5. The phase sensitive amplifier can be balanced by adjusting the relative intensities of the two beams and the phase of the reference signal. This may be achieved either by means of adjustment of the mirrors (2) and (3) or by allowing the laser output to go through the methane cell 7 of variable pressure (or fixed pressure but variable path length). These adjustments allow balance of the phase-sensitive amplifier to a zero reading. After this, if a small trace of methane is introduced in the path of the output beam, it would lead to an imbalance in the lock-in output.

Referring still to FIG. 3 a variable-pressure methane cell 8 having pressure regulator 8a (or a variable pressure applying bellows) is provided at the laser output for balancing the bridge. Detecting device 10 sees a signal off beam-splitter 9. With switch 14 in position (a), the phase-sensitive amplifier is balanced. Then switch 14 is shifted to position (b) for reading the signal due to methane absorption. The absorption path-length outside of the laser can be a folded path (using reflecting mirrors). For one meter path-length, this system will have detection sensitivity better than one part in a million of methane concentration in the atmosphere.

Figure 4:
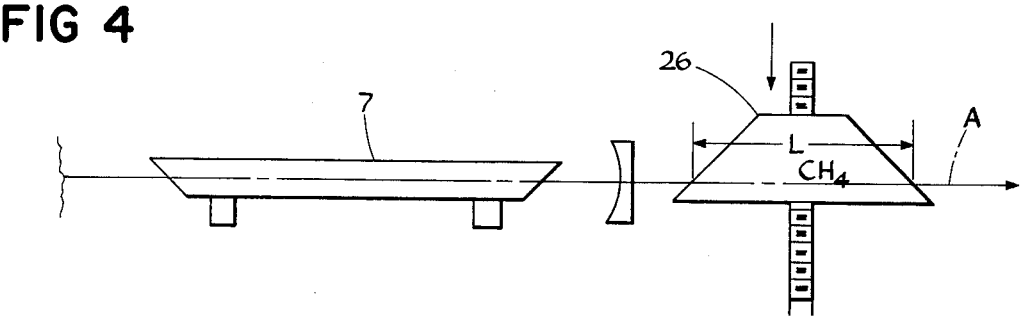
FIG. 4 is a view of an alternate adjustment cell for use in the embodiment of FIG. 3.

Referring to FIG. 4 an alternate cell 28 comprises a tube having opposite ends set at opposite Brewster angles. Movement of the cell transversely to the axis A, see the arrow, changes the effective length L of the cell.

Figure 5:
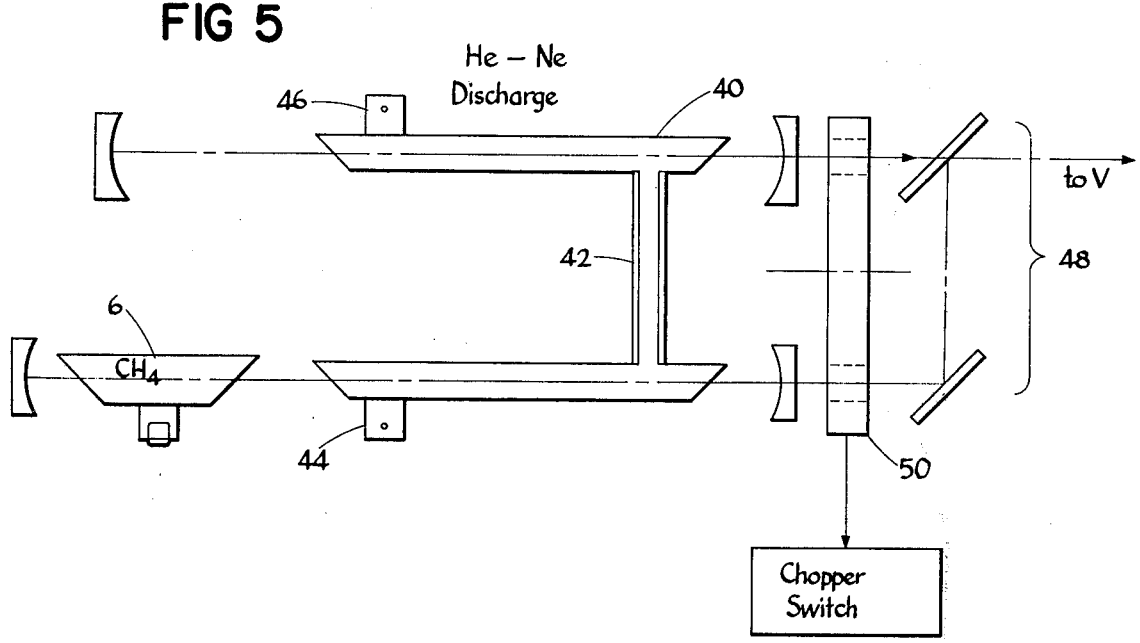
FIG. 5 is a block diagram of another preferred embodiment incorporating two separate laser cavities with a common pressure lasing medium.

Type II trace gas detector:

Referring to FIG. 5, in this system the $3s_2 \rightarrow 3p_4$ resonator 40 is separate from the $3s_2 \rightarrow 3p_2$ resonator 42. However a passage 42 provides communication between the tubular enclosures of the two resonators, establishing the same pressure of the He-Ne mixture in each. Cathode 44 is associated with one resonator and anode 46 with the other, thus defining a single discharge tube which allows the same unavoidable drift and fluctuation due to discharge instability, etc., to appear at both beams. The two beams are then combined outside of the laser by beam combiner optics 48. A mechanical or electro-optical chopper switch 50 alternately modulates the two beams, allowing them to appear 90° out of phase at the output. The remainder of the detection system can be the same as shown in FIG. 3.

Figure 6:
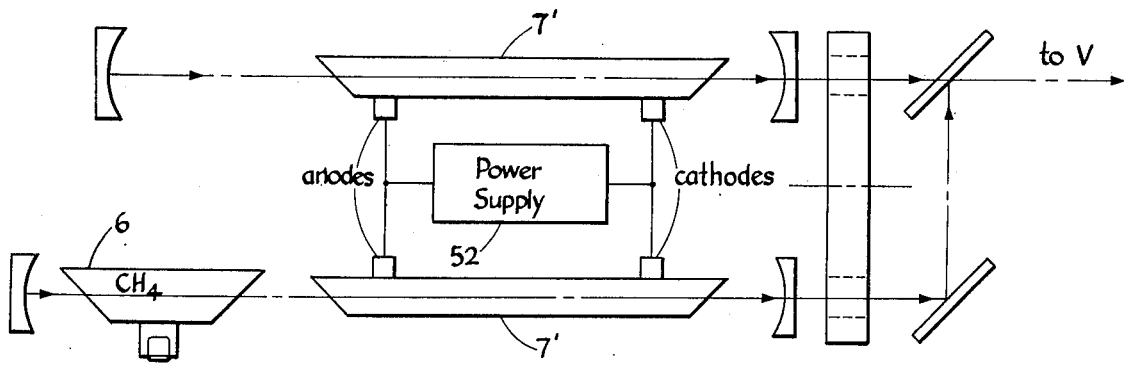
FIG. 6 is a block diagram of still another embodiment.

Type III trace gas detector:

Referring to FIG. 6, in this type of detector, two separate He-Ne lasers are used, sharing a power supply 52. One of them contains the methane cell 7, forcing it to oscillate on the $2s_2 \rightarrow 2p_2$ transition. The reset follows as in Type II and in Type I.

In a dual-beam system of the type described above, still another method is to produce the beam at the shifted frequency by placing the laser in a magnetic field provided by means of a solenoid. The laser frequency will be shifted due to Zeeman effect when the magnetic field is switched on.

In still another embodiment the second beam can be produced by generating a side band of the first beam and the transmitted beams can be detected employing a local oscillator, a mixing element such as a metal-oxide-metal diode system and i.f. detection circuitry. In this case both can transit the same path and be energized continuously, with separate i.f. detectors tuned to detect the respective beat signals and apply them to the balance circuitry.

In general it is preferred that the second beam, no matter how generated, be separated at least one-half of the line width from the first beam, but preferably no more than about 5 times the line width, thus to assure similar effects from scattering particles and the like.

What is claimed is:

1. In a detector for a prespecified gas having a given absorption resonance for optical radiation comprising laser means for producing first and second beams, said first beam having a first wavelength corresponding to said resonance and said second beam having a second wavelength relatively close to that of said second beam but outside the effective absorption curve of said gas, means arranged to cause said beams to transit a volume through which optical scattering particles may pass and in which said gas to be detected may be present, to enable absorption of said first beam, detection means for detecting said beams after said transit and comparison means for comparing said detected beams and producing an output indicating the presence or absence of said gas in said volume, the improvement wherein the laser means comprises a predetermined lasing medium selected to have two characteristic lines corresponding to said first and second wavelengths and two distinct resonant lasing cavities employing said lasing medium for producing said beams, said lasing cavities including at least one common operative means subject to variation, both beams thereby being similarly affected by said variation, and switching means for causing alternating pulses of said two beams to pass colinearly from said laser means via a common path through said volume to a commpon detecting device, said means for alternating said pulses operable with a period less than the period of transit of scattering particles through said volume whereby both beams are similarly affected by said particles.

2. The detector of claim 1 wherein said two lasing cavities employ a common lasing medium for generating said two beams and means to establish different lasing conditions in respect of said two beams thereby to produce their respective wavelengths.

3. The detector of claim 2 wherein said two laser cavities share a common output mirror through which their outputs pass to said common path through said volume in alternate fashion responsive to said switching.

4. The detector of claim 2 including a common power source for energizing said laser medium irrespective of which cavity is operable and a selective suppressor in at least one of said cavities adapted to suppress a wavelength that tends to be dominant under unrestricted lasing conditions thereby establishing a beam of selected different wavelength.

5. The detector of claim 2 wherein said lasing medium is a gas, said gas communicating with two different regions, each region associated with a different resonant cavity corresponding to a respective beam, said communication establishing substantially balanced pressure conditions within said two regions whereby variations in gas pressure produce related variations in the two beams.

6. The detector of claim 1 wherein said two cavities respectively produce said two beams along different paths and beam combiner optics are provided whereby each beam is directed along said common path.

7. The detector of claim 6 wherein each of said cavities contains the same kind of lasing medium and a selective suppressor in at least one of said cavities adapted to suppress a wavelength that tends to be dominant under unrestricted lasing conditions, thereby establishing a beam of selected different wavelength.

8. The detector of claim 7 having a common power source for energizing the laser medium in each of said cavities to lasing level.

9. In a detector for a prespecified gas having a given absorption resonance for optical radiation comprising laser means for producing first and second beams, said first beam having a first wavelength corresponding to said resonance, and said second beam having a second wavelength relatively close to that of said second beam but outside the effective absorption curve of said gas, means arranged to cause said beams to transit a volume in which said gas to be detected may be present, to enable absorption of said first beam, detection means for detecting said beams after said transit and comparison means for comparing said detected beams and producing an output indicating the presence or absence of said gas in said volume, the improvement wherein two distinct resonant lasing cavities are defined having a predetermined common volume of lasing medium selected to have two characteristic lines corresponding to said first and second wavelengths, and switching means for enabling alternate activation of said different cavities, said cavities sharing a common mirror through which their outputs pass colinearly to said common path through said volume in alternate fashion responsive to said switching, and said detection means comprises a common detecting device for alternately responding to said two beams.

10. The detector of claim 9 including a common power source for energizing said laser medium irrespective of which cavity is operable and a selective suppressor in at least one of said cavities adapted to suppress a wavelength that tends to be dominant under unrestricted lasing conditions thereby establishing a beam of selected different wavelength through said mirror.

11. In a detector for a prespecified gas having a given absorption resonance for optical radiation comprising laser means for producing first and second beams, said first beam having a wavelength corresponding to said resonance, and said second beam having a wavelength relatively close to that of said second beam but outside the effective absorption curve of said gas, means arranged to cause said beams to transit a volume in which said gas to be detected may be present to enable absorption of said first beam, detection means for detecting said beams after said transit and comparison means for comparing said detected beams and producing an output capable of indicating the presence or absence of said gas in said volume, the improvement wherein said laser means comprises a predetermined lasing medium for each of said beams having a given upper energy state and two relatively closely spaced lower energy states one of which tends to dominate, lasing action being possible by transition between said upper state and each of said lower states to produce respectively said first and second wavelengths, and means operable to establish, for producing each detector beam, a respective different one of said transitions in said lasing medium, said means comprising two distinct resonant lasing cavities for the respective beams, the cavity for said second beam containing a suppression cell filled with gas having the absorption characteristic of the prespecified gas to be detected.

12. The detector of claim 11 wherein a first of said transitions tends to be dominant under unrestricted lasing conditions and tends to suppress the second of said transitions, and said means operable to establish said second transition comprising a selective suppressor adapted to preferentially absorb radiation corresponding to said first transition to the extent that lasing at said second transition becomes dominant.

13. The detector of claim 11 including a common power source for energizing said lasing medium at each of said transitions.

14. The detector of claim 11 wherein said lasing medium is a lasing gas and wherein the pressure of the gas in the two lasing actions is correlated.

15. The detector of claim 11 wherein said lasing medium is a mixture of helium and neon, said upper state is the $3s_2$ state of neon and said lower states are the $3p_4$ and $3p_2$ states of neon, the transition $3s_2$ to $3p_4$ being normally dominant, and said absorber comprising a quantity of methane in the optical cavity producing said second beam.

16. A methane detector, methane having a given absorption resonance for optical radiation of 3.39 micron wavelength, said detector comprising helium-neon laser means having means for energizing the $3s_2$ state of neon, means comprising two distinct lasing cavities to produce respectively a first beam by the transition $3s_2$ to $3p_4$ and to produce a second beam by the transition $3s_2$ to $3p_2$, switching means for causing each of said beams to transit a volume in which methane to be detected may be present, said first beam having a wavelength corresponding to said resonance and the wavelength of said second beam being close to but outside the effective absorption curve of methane, detection means for detecting each of said beams after said transsit and comparison means for comparing said detected beams and producing an output capable of indicating the presence or absence of methane in said volume.

17. The methane detector of claim 16 wherein said means to produce said second beam includes a transparent cell containing a predetermined quantity of methane, said cell disposed in a laser cavity and serving as an absorber, suppressing the $3s_2$ to $3p_4$ transition and allowing the $3s_2$ to $3p_2$ transition to oscillate with its radiation passing freely through said cell.

18. The methane detector of claim 17 including a transparent balancing cell through which said first beam passes, said cell containing methane and arranged to enable variation of the number of methane molecules in the path of said beam thereby to enable said beam intensity to be varied prior to transit through said volume to enable balancing of the intensity of the first beam relative to that of the second beam.

19. The methane detector of claim 18 wherein the pressure of methane within said cell is variable to enable balancing of the detector.

20. The methane detector of claim 18 wherein a common path of said first and second beams extends through said cell thence through said volume.

* * * * *